(12) United States Patent
Changaris et al.

(10) Patent No.: US 11,197,824 B2
(45) Date of Patent: Dec. 14, 2021

(54) SOLUTION AND METHOD FOR REDUCING THE VIRULENCE OF VIRUSES, BACTERIA, YEASTS, OR FUNGUS

(71) Applicants: David G. Changaris, Louisville, KY (US); Anne L. Carenbauer, Louisville, KY (US)

(72) Inventors: David G. Changaris, Louisville, KY (US); Anne L. Carenbauer, Louisville, KY (US)

(73) Assignee: David Changaris, Louisville, KY (US)

( * ) Notice: Subject to any disclaimer, the term of this patent is extended or adjusted under 35 U.S.C. 154(b) by 60 days.

(21) Appl. No.: 16/938,753

(22) Filed: Jul. 24, 2020

(65) Prior Publication Data
US 2021/0299043 A1 Sep. 30, 2021

Related U.S. Application Data

(60) Provisional application No. 63/003,249, filed on Mar. 31, 2020, provisional application No. 62/961,994, filed on Jan. 16, 2020.

(51) Int. Cl.
| | |
|---|---|
| *A61K 9/08* | (2006.01) |
| *A61K 31/19* | (2006.01) |
| *A01N 37/06* | (2006.01) |
| *A61K 9/00* | (2006.01) |

(52) U.S. Cl.
CPC ........... *A61K 9/08* (2013.01); *A01N 37/06* (2013.01); *A61K 31/19* (2013.01); *A61K 9/0014* (2013.01); *A61K 9/0019* (2013.01); *A61K 9/0034* (2013.01); *A61K 9/0043* (2013.01); *A61K 9/0048* (2013.01); *A61K 9/0053* (2013.01); *A61K 9/0082* (2013.01)

(58) Field of Classification Search
CPC ..... A61K 31/201; A61K 31/231; A61P 31/00; A61P 31/02; A61P 31/04
See application file for complete search history.

(56) References Cited

U.S. PATENT DOCUMENTS

| | | | | |
|---|---|---|---|---|
| 4,997,851 A * | 3/1991 | Isaacs | | A61K 31/20 |
| | | | | 514/558 |
| 9,549,550 B2 * | 1/2017 | Changaris | ........... | A61K 9/0014 |
| 9,962,354 B2 * | 5/2018 | Changaris | ........... | A01N 37/06 |
| 10,105,332 B1 * | 10/2018 | Changaris | ........... | A61K 31/201 |
| 2013/0131172 A1 * | 5/2013 | Zhang | ........... | C07C 57/03 |
| | | | | 514/560 |
| 2016/0100577 A1 * | 4/2016 | Salminen | ............... | A01N 37/02 |
| | | | | 514/517 |
| 2017/0079945 A1 * | 3/2017 | Changaris | ........... | A61K 9/0014 |

OTHER PUBLICATIONS

Blair et al. (F1000 Research, 2016, vol. 5, pp. 1-7) (Year: 2016).*
Boyce (Antimicrobial Resistance and Infection Control, 2016, vol. 5, 1-10) (Year: 2016).*
Jang et al (Journal of Applied Microbiology, 2015, vol. 120, pp. 280-288) (Year: 2015).*

* cited by examiner

*Primary Examiner* — Mark V Stevens
(74) *Attorney, Agent, or Firm* — Witters & Associates; Steve Witters

(57) ABSTRACT

A method of reducing the virulence of microbes in or on the human body and a method of sanitizing or disinfecting a surface, area, object, or porous or non porous material is provided. The methods comprise applying or injecting a solution having an effective amount of a conjugated diene for substantially reducing the virulence of the microbes or sanitizing or disinfecting a surface, area, object, or porous or non porous material.

18 Claims, 2 Drawing Sheets

SOLUTION AND METHOD FOR REDUCING THE VIRULENCE OF VIRUSES, BACTERIA, YEASTS, OR FUNGUS

CROSS REFERENCE TO RELATED APPLICATIONS

This application claims priority to U.S. provisional application No. 63/003,249, filed Mar. 31, 2020, the disclosures of which is hereby incorporated by reference in its entireties.

FIELD OF THE DISCLOSURE

The present disclosure relates to solutions and methods for reducing the virulence of microbes.

BACKGROUND

Microbes such as viruses, bacteria, yeasts, and fungus have been the cause sicknesses, hospitalizations, and deaths. They are also responsible for large costs in terms of health care, drugs, and for the indirect costs due to non-attendances at work and schools. A recent example of large costs incurred by society with such microbes is the SARS CoV 2 (COVID-19) pandemic.

The spread of microbes may become epidemic in nature and may cause deaths, especially among vulnerable individuals such as the elderly and children and in immunosuppressed individuals.

The microbes may cause respiratory infections. In a survey conducted in the United States in 1995, infections of the upper respiratory ways were the main cause of medical examination before the General Practitioner's and Emergency clinics, with 37 million medical examinations and 52% of patients with uncomplicated upper respiratory infections, treated with antibiotics according to the "National Ambulatory Medical Care Survey".

The most widely used method of treatment of respiratory infections is the administration of antibiotics, and in many cases, antibiotics are administered without a real and actual need and may even have detrimental effects on the patient, It may be desired to provide solutions and methods for reducing the virulence of microbes.

SUMMARY

In one aspect of the present disclosure, a method of reducing the virulence of microbes in or on the human body is provided. The method comprises applying a solution to at least one of a mouth, nasal cavities, lungs, eyes, skin, and vagina, or injecting a solution intravenously, wherein the solution comprises an effective amount of a conjugated diene for substantially reducing the virulence of the microbes.

In another aspect of the present disclosure, a method of sanitizing or disinfecting a surface, area, object, or porous or non porous material is provided. The method comprises applying an effective amount of a conjugated diene to the surface, area, object, or porous or non porous material.

BRIEF DESCRIPTIONS OF THE DRAWINGS

Figure 1:
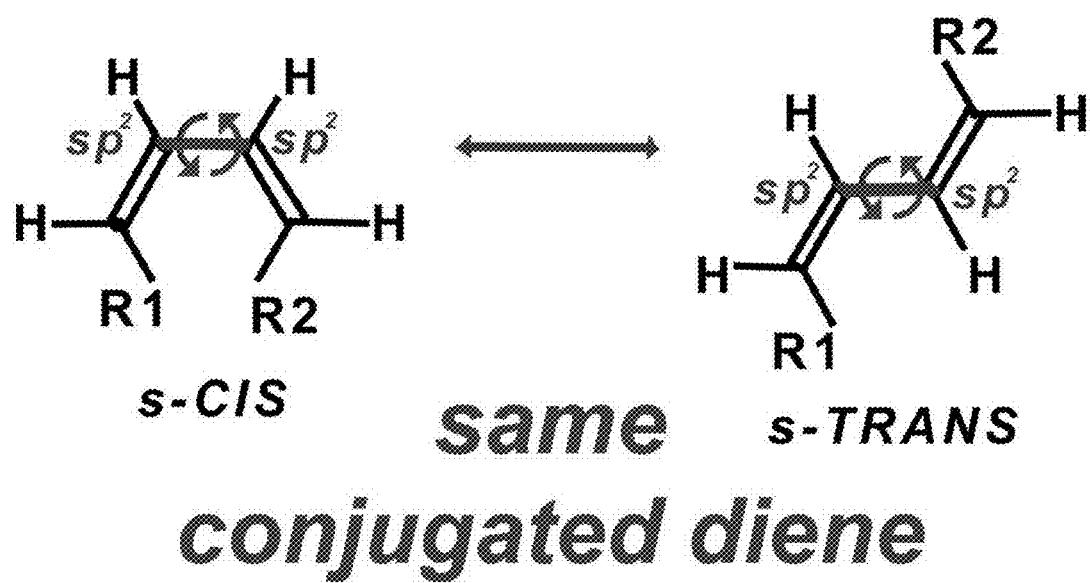
Figure 2:
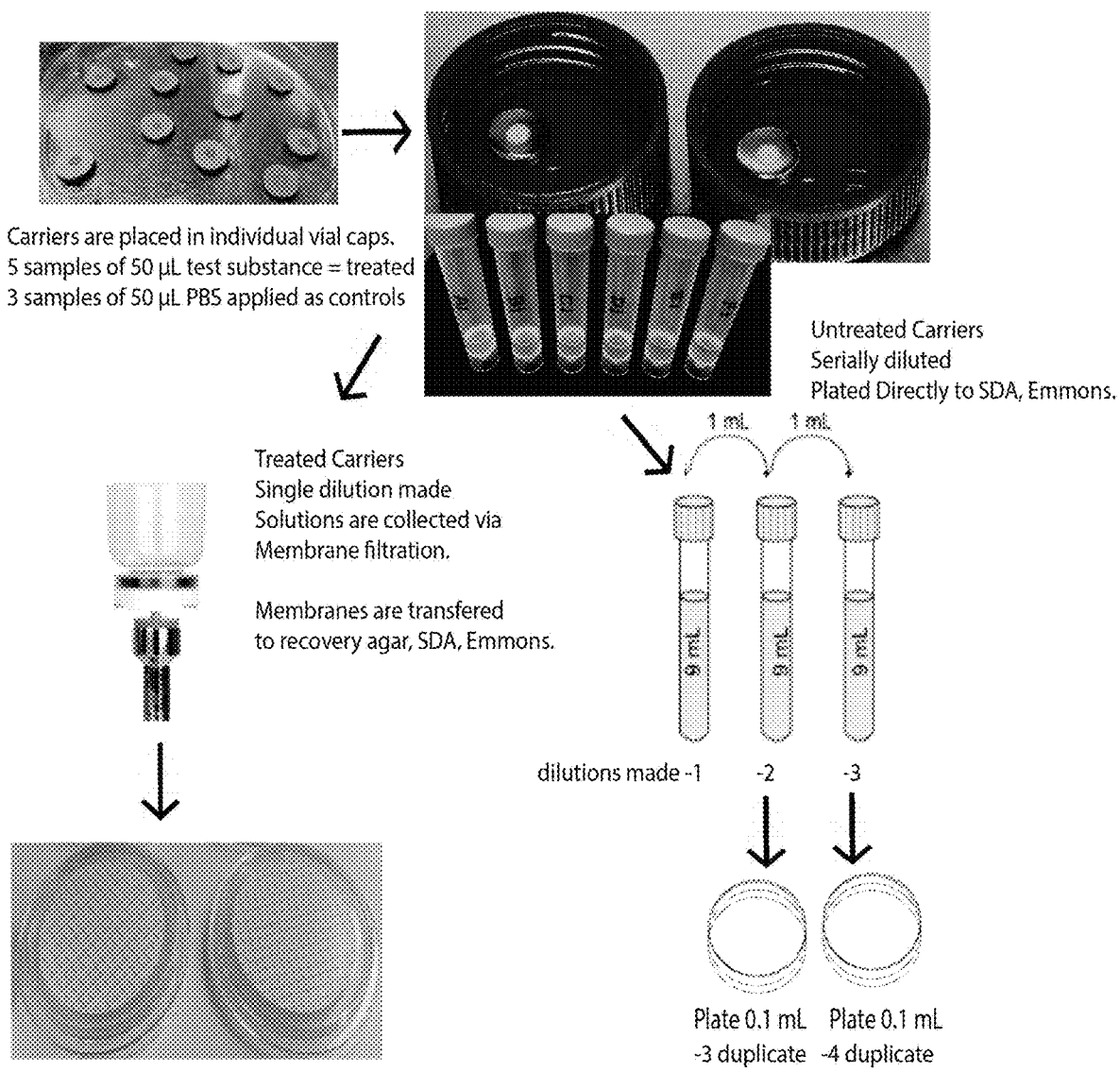

The foregoing and other features of this disclosure will become more fully apparent from the following description and appended claims, taken in conjunction with the accompanying drawings and examples. Understanding that these drawings depict only several embodiments in accordance with the disclosure and are, therefore, not to be considered limiting of its scope, the disclosure will be described with additional specificity and detail through use of the accompanying drawings, in which:

FIG. 1 shows an illustrative example of a conjugated diene that may be used in the presently disclosed solution and method for reducing the virulence of microbes; and FIG. 2 illustratively shows a test method of Example 1.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In at least one embodiment of the present disclosure, a method of reducing the virulence of microbes in or on the human body is presently disclosed. The method comprises applying a solution to at least one of a mouth, nasal cavities, lungs, eyes, skin, and vagina, or injecting a solution intravenously, wherein the solution comprises an effective amount of a conjugated diene for substantially reducing the virulence of the microbes.

The effective amount of the conjugated diene may block cell penetration of microbes by adhering to hydrophobic structures made further electron poor by basic amino acids or other chemicals in the viral envelope. This may include the spike protein of SARS CoV 2 (COVID-19) and other viruses and microbes that involve similar structures.

The conjugated diene, for example conjugated linoleic acid, may poses two structure-activities for attaching to hydrophobic electron poor structures to alter cell function, cause apoptosis or sequester small molecules or portions of larger molecules. As used herein, the term conjugated diene includes, but is not limited to, conjugated linoleic acid and isomerized linoleic cationic salts (ILCS). The first structure activity may be a centrally located conjugated diene and the second structure activity may be two aliphatic arms of sufficient length with capacity to rotate about the $sp^2$-$sp^2$ bond, from trans to cis and to attach and hold structures by hydrogen bonds. For example, FIG. 1 may show an illustrative example of a conjugated diene that may be used in the presently disclosed solution and method for reducing the virulence of microbes.

The conjugated diene may have one arm with a carboxyl group or an acidic moiety or an electronegative element such as a cation and the other arm may have an aliphatic chain. The two arms may trap hydrophobic regions such as tryptophan or phenylalanine on microbial surfaces or molecules thru a combination of electrostatic, orbital, and steric forces.

For example, the conjugated diene of the present disclosure may have a structure of R1-C=C-C=C-R2, wherein R1 and R2 each have at least one carbon. In at least one embodiment, R1 may have an aliphatic chain and R2 may have a carbon chain and a carboxyl group or an acidic moiety.

Hydrophobic structures may anchor many microbes to mammalian cells and the conjugated diene may target these anchors to limit their virulence. Since the SAR CoV S1 spike protein has both tryptophan and phenylalanine within its anchoring portions and sequence homologies to SAR CoV 2, the conjugated diene may bind with these sites to limit viral anchoring. Such a process may block propagation of the viruses to adjacent or distant epithelia within an airway. This may in turn slow the progression of symptoms until the host develops sufficient immunity to prevent systemic progression.

The application of the solution having an effective amount of a conjugated diene in a pharmacologically acceptable vehicle may limit or reduce the virulence of the microbes. An effective amount of the conjugated diene in the pharmacologically acceptable vehicle may be at a concentration of the conjugated diene between 0.1 millimolar and 500 millimolar, between 0.2 millimolar and 60 millimolar, between 1 millimolar and 100 millimolar, between 1 millimolar and 10 millimolar, between 1 millimolar and 5 millimolar, or between 5 millimolar and 10 millimolar.

Conjugated diene may disorder the capacity of *P. aeruginosa* Quorum Sensing Agents to initiate slime formation at dilutions that permit *P aeruginosa* growth. This interference of Quorum Sensing Agents with the conjugated diene may occur in a range of concentration of the conjugated diene in the pharmacologically acceptable vehicle between about 1 millimolar and 10 millimolar. This inhibition of slime formation with the conjugated diene may provide for limiting the expression of virulence in the gut microbiota and other microbiomes.

In at least one embodiment, the conjugated diene has isomerized linoleic cationic salts (ILCS), a C18 conjugated diene aka "conjugated linoleic acid". ILCS is generally recognized as safe and exposure to humans may pose little or no risk beyond local discomfort. ILCS may have broad spectrum lethality to viruses, gram positive and gram negative bacteria, yeast and fungi. ILCS may have antimicrobial efficacy which may included antibiotic resistant bacteria such as methacillin resistant *staphylococcus* and vancomycin resistant *enterococcus* (Changaris, 2018; Changaris and Sullivan, 2019). For example, ILCS may have lethality to *Aspergillis brasiliensis*.

An ILCS cleanser may provide a cosmetically acceptable experience for bathing, washing hair, mucous membranes and barrier deficient skin (Changaris, 2020). While generating cosmetic formulations of a conjugated diene potassium salt, ILCS may form a hard gel. This gel may solidify over days to weeks. Cosmetically acceptable carriers may include non GMO plant oils, aminos, and vitamins. Higher concentrations of ILCS may form increasingly viscous gels with changes in color.

Certain amino acids may increase the viscosity of gels, while others reduce or even possibly increased the hydro-gel tension. Additionally, those amino acids may change the color of the gel. We have deduced that these changes may reflect conformational changes interacting with the conjugated structure deep within the ILCS, and in fact, these amino acids, when minimally modified, are similar to QSAs. This relaxation and color effect may be caused by structures similar to a Quorum Sensing Agents (QSAs), amino acids with correlative QSA of gram positive and negative bacteria as well as fungi and yeasts (Sprague, 2006) or plant communicating molecules (Ding and Ding, 2020). QSAs may provide for the interactions between ILCS and viruses, gram positive and gram negative bacteria, yeast and fungi, and the mechanism of inhibition and cidal activity. These amino acids are hydrophobic and rich in electron-poor moieties. ILCS possesses a hydrophobic aliphatic arm and a hydrophilic one with a single carboxyl group. The centrally located conjugated diene may serves to anchor electron poor hydrophobic structures and limit quorum sensing activities. This may have the effect of blocking communication between microbes, defined by quorum sensing.

It is known that the conjugated diene rotates around the single carbon bond between the two dienes (Ashenhurst, 2020). This rotation maintains a dynamic equilibrium between the s-cis and s-trans without breaking the molecular bond. Any given conjugated diene molecule may maintain a dynamic equilibrium between s-cis and s-trans as shown in FIG. 1. This unique shared sp2-sp2 pi orbitals, in connection with the long aliphatic arms, combined, may generate strong and rapid interactions with quorum sensing molecules and surface amino acids.

The sp2-sp2 pi bond may allow the s-trans to rotate into the s-cis position after attracting an electron poor hydrophobic portion of a molecule such as histidine, proline, tryptophan, phenylalanine, lactones, or hydrophobic moieties. With a multi-carbon chain on either side of the sp2-sp2 bond, the arms may rotate from s-trans towards s-cis positions. The arms may fit around amino acids, peptide-sized molecules, or "squeeze" cell surfaces which may hold amino acids and peptide-sized molecules. Many QSAs have hydrophobic electron poor components that can fit here. The transition back and forth between the s-cis and s-trans configurations may permit the molecule to trap molecules or regions of larger molecules. The cation salt of the carboxyl group may tend to "lock" a molecule with the "right" conformation in place. The presence of mixed isomers of C18 linoleic acid may enhance the range of molecules that might be trapped by this mechanism.

In at least one embodiment of the present disclosure, a method of reducing the virulence of microbes in or on the human body comprises applying a solution to at least one of a mouth, nasal cavities, lungs, eyes, skin, and vagina, or injecting a solution intravenously. The solution has an effective amount of a conjugated diene for substantially reducing the virulence of the microbes.

The conjugated diene may have a structure of R1-C=C-C=C-R2 as shown in FIG. 1. R1 has at least one carbon and R2 has at least one carbon. R1 may have an aliphatic chain and R2 may have a carbon chain and a carboxyl group or an acidic moiety. The conjugated diene may have up to 40 carbons. For example, the conjugated diene may have between 8 carbons and 30 carbons. The aliphatic chain in R1 may have between 3 carbons and 13 carbons. For example, the aliphatic chain in R1 may have between 6 carbons and 9 carbons. The carbon chain in R2 may have between 2 carbons and 15 carbons. For example, the carbon chain in R2 may have between 4 carbons and 5 carbons.

Corona viruses have received significant attention as they infect many animals causing significant animal husbandry issues. Over the last three decades three corona viruses have transcended the animal to human host to cause substantial deaths to the human population. The latest remains the SARS COV 2 (following MERS and SARS COV). A great deal of attention has been focused on the spike protein (S) of the corona viruses. SARS Cov and SARS Cov 2 appear to have preserved the hydrophobic amino-acid-anchoring tool, using tryptophan and likely phenylalanine buried in an S spike protein, also rich in basic amino acids.

Isomerized linoleic cationic salts, conjugated diene, or conjugated linoleic acid may block viral fusion by selectively binding the S-spike-protein-anchor tryptophan and other hydrophobic amines. The spike protein of SARS CoV 2 (COVID-19) and other viruses and microbes may use such structures as "docking" points to initiate cell entry. ILCS may have the capacity to block viral fusion by binding to these docking points.

The spike or S protein remains the main focus of neutralizing antibody study and vaccine design (Tortorici and Veesler, 2019). Detailed analysis the S1/S2 spike region allows review of surface amino acid sequencing and comparison through many corona species (Walls et al., 2020). Analysis of the S protein has led to mechanisms for antibody synthesis and drug interventions to disrupt some aspect of the viral intrusion process. The analysis of the Data S1. Amino Acid Sequence Alignment of Sarbecovirus S Glycoproteins (Walls et al., 2020) approximately 1273 amino acids shows this collection contains 40% hydrophobic amino acids and 9% basic amino acids. With nearly 50% of the S1/S2 amino acid composition defined this way it may be reasonable that some of these hydrophobic structures would be both hydrophobic and electron poor due to proximity to the basic regions. Some investigations have shown specifically that tryptophan performs function as an initial anchor with a quaternary structure that may be wrapped by ILCS, making this anchor unavailable. For example, Alpha-CoV has recognition of cell entry receptors in she form of tryptophan. Conjugated diene, ILCS, or conjugated linoleic acid may wrap the tryptophan anchor, making it inaccessible to the cell entry receptors.

Tryptophan and phenylalanine together make up 7% of the Data 1 set of SAR Cov-2 (Walls et al., 2020). They produce rapid changes in the viscosity of ILCS. This suggests ILCS may have an attraction for tryptophan or phenylalanine residues especially when adjacent to basic structures. Given the number of these amino acids some would likely be on the surface or superficial enough to become open as the ILCS moves toward it. SAR COV 2 may enter the cell through angiontensin converting enzyme 2 (ACE-2), a ubiquitous cathepsin mono-peptidase attached to the cell membrane. This enzyme would need to attract at least 4 carboxyl amino acids to cleave sequentially the first two amino acids in the angiotensin I sequence Asp-Arg-Val-Tyr-Ile-His-Pro-Phe-His-Leu Val-Ile-amino acids. These amino acids may disorder the viscosity of ILCS.

Potassium hexadiene (pH 9) was shown to have little reduction in microbial growth as compared to ILCS efficacy of 8-10 log reduction, indicating that the aliphatic and carboxylic arms participate in microbial lethality. The long flexible arms of ILCS may create a non-destructive hydrophobic pocket around the conjugated diene, much like Diels-Alderase creates an active site pocket (Oikawa, 2016).

Low concentrations 3-10 mM of ILCS may be effective for inactivating virus populations. ILCS, conjugated linoleic acid, or conjugated diene is generally recognized as safe by the FDA. The aerosolizing of millimolar concentrations of conjugated diene may provide for delivery to nasal and oral cavities as well as trachea and lungs which may be effective in reducing the virulence of microbes. ILCS alone may have a salutary effect on mobilizing mucous when coupled with postural drainage during pulmonary therapy. The basic nature of the ILCS solution may drive the local pH towards 8, where rapid viral inactivation of some corona species has been reported in vitro (Sturman et al., 1990).

Corona viruses possess an array of peplomers with hydrophobic amino acids that suggests ILA (Isomerized Linoleic Acid), conjugated diene, conjugated linoleic acid, or ILCS may encase these and interfere with fusion to host cells. ILCS preparations at pH 7-10.5 remain soluble and effective at killing a wide range of microbes to pH 7.8-8.0 when diluted with artificial hard-water. The ILCS preparations have a pH of 9-10.5 and we know that some corona virus species are inactivated at or above pH 8 (Sturman et al., 1990).

A 2-50 mM ILCS spray or wash for the nasopharynx cavity has reduced symptoms associated with viral illnesses such as pharyngitis and rhinorrhea. With respect to pharyngitis, for a significant minority, a topical application of a low concentration of xylocaine helps severely sore throats with the first few gargles or spray applications. After these initial treatments xylocaine is rarely needed.

In at least one embodiment, the disclosed method of reducing the virulence of microbes in or on the human body comprising applying a solution to at least one of a mouth, nasal cavities, lungs, eyes, skin, and vagina, or injecting a solution intravenously, wherein the solution comprises an effective amount of a conjugated diene for substantially reducing the virulence of the microbes. The solution may further comprise at least one of water, amino acid, cations, and alcohol. For example, the solution may comprise the cations at least at a substantially molar equivalent to the conjugated diene in the solution.

The cations may have at least one of lithium, sodium, potassium, and rubidium. In at least one embodiment, the solution has sodium. In at least one other embodiment, the solution has potassium. The solution may comprise the cations at a molar ratio of the cations to the conjugated diene between about 1:1 and 5:1.

The solution may have a concentration of the conjugated diene between 0.1 millimolar and 500 millimolar, or between 0.2 millimolar and 60 millimolar.

In at least one embodiment, the disclosed method of reducing the virulence of microbes includes reducing the virulence of gram positive bacteria, gram negative bacteria, virus, fungus, yeast, or combinations thereof. The microbes may have a microbial surface containing at least one region having greater than 10% of histidine, proline, tryptophan, phenylalanine, lactones, or hydrophobic moieties. These lipid structures may provide a site for the binding of ILCS, and thereby reduce the virulence of the microbes. The presently disclosed method of reducing the virulence of microbes may provide for a substantial reduction of the virulence of the microbes in less than 60 seconds.

In at least one embodiment of the present disclosure, a method of sanitizing or disinfecting a surface, area, object, or porous or non porous material is provided, The method comprises applying an effective amount of a conjugated diene to the surface, area, object, or porous or non porous material. For example, an effective amount of conjugated diene may be sprayed, wiped, or otherwise applied onto the surface, area, object, or porous or non porous material that is being treated.

EXAMPLES

Example 1

Long-standing regulatory perspectives hold that all plant-oil soap salts lack direct antimicrobial capacity. We demonstrate that the potassium salt of isomerized linoleic acid [UNIT: 70S2158RCI], a plant-oil soap and conjugated diene, at 0.42 M exceeds the required 5 log kill rate for the invasive antifungal-resistant *Candida auris* (AR-0381) within 1 min by in vitro testing to fulfill the US EPA standards for *C. auris* disinfection. Testing this plant salt against *Candida albicans* (ATCC 10231) also demonstrated greater than 5 log kill rates at 1 min.

Current regulatory guidance from the Environmental Protection Agency (EPA) states: "In 1988, the EPA determined that soap salts have 'no independent pesticidal activity' in antimicrobial products, and must be classified as inert ingredients in those products (see 40 CFR 153.139). Antimicrobials that still contain soap salts as active ingredients are considered misbranded (US Environmental Protection Agency. 1992).

Since this determination in 1992, studies published within the US patent literature have indicated that isomerized linoleic plant salts have broad-spectrum lethality toward gram-positive and gram-negative bacteria, yeast, and fungi (Changaris. 2018: Changaris and Sullivan. 2019). The reported antimicrobial efficacy included antibiotic-resistant bacteria, such as methicillin resistant *staphylococcus* and vancomycin-resistant enrero coccus, as well as *Candida albicans* (Changaris. 2018). It appeared to us that the mechanism of action may be outside of the known mechanisms classically used by microbes to develop resistance (Reygaert. 2018).

Consequently, we tested potassium-isomerized linoleic acid against the invasive antifungal-resistant *Candida auris* (AR-0381). The CDC identifies *C. auris* as a major threat to the world because immunocompromised individuals suffer fatality rates ranging from 10% to 60% (Lockhart et al. 2017). The resistance pattern of the isolate (AR Isolate Bank #0381), shown in Table 1, supports their perspective. The genome sequence is available in the AR Isolate Bank as Biosample Accession #5AMN05379608 (CDC, 2016).

TABLE 1

Antimicrobial Sensitivities for *Candida auris*, (AR-0381)

| Drug | MIC (µg/mL) |
|---|---|
| Amphotericin 81 | 0.38 |
| Anidulaftrngin | 0.25 |
| Caspofungin | 0.13 |
| Fluconazole | 4.00 |
| Flucytosine | 2.00 |
| Iuaconazole | 0.13 |
| Micafungin | 0.13 |
| Posaconazole | 0.06 |
| Voriconazole | 0.03 |

We used EPA protocol MB-35-00 for testing disinfectants against *C. auris* (US Environmental Protection Agency. 2017, 2020) and *C. albicans* ATCC 10231, a yeast common in package spoilage of food and cosmetics.

Potassium hexadiene contains the central four-carbon conjugated diene structure absent the carbon arms of potassium-isomerized linoleic acid. To identify whether the conjugated carbons by themselves are sufficient, we tested this compound using the same protocols.

Materials and Methods

ILCS Production

We prepared potassium-isomerized linoleic acid using potassium hydroxide purchased from Spectrum Chemical (New Brunswick Ni USA) and isomerized linoleic acid from Quanao Biotech Co., Ltd. (Shaanxi. China) and Stepan Co. (Northfield. Ill., USA). We also prepared and tested the salt using in-house isomerized linoleic acid prepared from safflower purchased from Jedwards (Stockton. Mass. USA). The final solution contained 0.42 M potassium-isomerized linoleate, 15 mM aspartic acid, and 2.2 M ethanol. We tested 5 batches produced with difference sources of isomerized linoleic acid (Test Substances 1-5).

Antimicrobials against *C. auris*: MB-35-00 (US Environmental Protection Agency, 2017, 35-40)

The EPA test protocol for testing hard surface disinfection of *C. auris* (AR0381) with antifungal resistance includes an overnight culture of *C. auris* (AR.0381) shaken at 200 rpm at 30° C. From this culture, 8 mL was harvested by centrifugation, re-suspended in 2-3 mL phosphate-buffered saline (PBS), and mixed with a 3-part soil load including bovine serum albumin (BSA), yeast extract, and mucin. Metal carriers (10 mm) were inoculated (10 µL culture+soil load) and dried in a desiccator under vacuum (~70 min). The disk surface was coated with the test substance at 0.42 M (50 µL) for up to 10 min. Following incubation, the carriers were transferred to 10 mL neutralization solution (Sabouraud Dextrose Broth [SDB], a common yeast-mold growth media) for subsequent harvesting on membrane filters. The filtered membranes were transferred to Sabouraud Dextrose Emmons Agar (SDEA) plates to culture for 120 hours at 31° C. Controls consisted of PBS (50 µL) applied to inoculated metal disk carriers, subsequently transferred to 10 mL neutralization solution (SDB), diluted serially in PBS, and plated directly to SDEA plates, See FIG. 2.

Strains and Materials

*C. auris* (AR-0381): The CDC Isolate Bank (Atlanta, Ga., USA) graciously provided *C. auris* (AR-0381). This isolate has antimicrobial resistance to amphotericin B1, anidulaflingin, caspofungin, fluconazole, fiucytosine, itraconazole, micafungin, posaconazole, and voriconazole. The entire genomic sequence is available, and multiple resistance mechanisms are represented with this single isolate (CDC, 2016).

*Candida albicans* (ATCC 10231): We purchased *C. albicans* (ATCC 10231) from ATCC (Gaithersburg, Md., USA).

Test Carriers: We purchased flat metal carriers from Pegen Industries (part number #430-107L). We prepared and qualified these per EPA protocol (US Environmental Protection Agency, 2017).

Soil Stocks: We prepared soil stocks with yeast extract powder (Ref RM027) purchased from Himedia, BSA (A2153) purchased from Sigma Life Science, and gastric mucin (cat # HY-B2196/CS-7626) purchased from Mod Chem Express per SOP MB-35-00 (US Environmental Protection Agency, 2017).

Cell Harvesting: We removed cells from the growth culture media using a Micro-Centrifuge obtained from Changzhou Jintan Sanhe Instrument Co., LTD. (Model TGI6-W) at 10,000×g for 10 min in screw-top-cap vials purchased from Heathrow Scientific (Item HS 100600). The optical density of the inoculate was defined at 15-19 $OD_{600}$ in PBS with the Ultrospec 10 Cell Density Meter from BioChrom (Holliston, Mass., USA) prior to dilution in the soil load. Samples were diluted 1:10 in PBS to obtain absorbance readings between 1.5 and 1.9.

Membrane Filtration: Treated yeasts were collected using a combination of the Rocker (Cat #200300-01) and 47 mm PES membranes with a 0.45 micron pore size obtained from Sterlitech (Catalog # PE54547100). Magnets were used to hold the carriers in place during pouring.

SDEA, recovery agar: We purchased dextrose anhydrous (Item NCMO 121 6A), casein peptide type I (Item NCMO I 20A), and meat peptone no 3 (NCM0246A) from Neogen Culture Media (Lansing, Mich., USA). We purchased agar from Himedia (RM20I) (L.B.S. Marg, Mumbai, India).

Sabouraud Dextrose Agar, Emmons Modification per Liter:

| | |
|---|---|
| Dextrose | 20.0 g |
| Casein Peptone | 5.0 g |
| Meat Peptone | 5.0 g |
| Agar | 15.0 g |

Common Reagents

PBS: We generated stock solutions of PBS lox and PBS lx using sodium chloride (1528090) from Innovating Science (Avon, N.Y. USA), potassium chloride from Bearclaw Sales (Cooke City, Mich., USA), and sodium phosphate dibasic, anhydrous (89-1442) and potassium phosphate monobasic (884250) from Carolina Biological Supply Company (Burlington. N.C. USA).

Growth media/agars: We purchased SDB (Himedia Ref GM033) from Weber Scientific (Hamilton. N.J., USA) and CHROMagar *Candida* (Ref CA222) from local distributors.

Water for Injection: <USP1231>: Purified water that satisfies the USP Standards for endotoxin <USP85>, bulk water <USP645>, and total organic carbon <U5P643> were produced in house.

Results

Potassium-isomerized linoleic acid showed greater than 5 log kill rates for both *C. albicans* and *C. auris* for all carriers with two separately manufactured lots at 1 min. This satisfies the US EPA standards for *C. auris* disinfection (EPA. 2020). A 10-min test, the longest time allowed per the SOP, showed greater than 5 log kill rates. In fact, the kill rates ranged between 5 and 7 logs in all testing runs (Tables 2 and 3). Potassium sorbate kill rates on both organisms were limited to less than one log.

TABLE 2

*Candida albicans*

| Assay | Salt Batch | Exposure (min) | Control Disks | Density (log) | Test Disks | Density (log) |
|---|---|---|---|---|---|---|
| 1 | 1 | 10 min. | n = 2 | 6.2, 6.6 | n = 2 | All No Growth |
| 2 | 2 | 2 min. | n = 3 | 6.2, 6.1, 6.3 | n = 3 | All No Growth |
| | 3 | 2 min. | | | n = 7 | All No Growth |
| 3 | 4 | 2 min. | n = 3 | 6.6, 6.5, 6.6 | n = 7 | All No Growth |
| 4 | 4 | 1 min. | n = 3 | 5.2, 5.4, 5.4 | n = 5 | All No Growth |
| | 5 | 1 min. | | | n = 5 | All No Growth |
| Potassium Sorbate | | 1 min. | | | n = 2 | 4.8, 4.9 |

TABLE 3

*Candida auris*

| Assay | Salt Batch | Exposure (min) | Control Disks | Density (log) | Test Disks | Density (log) |
|---|---|---|---|---|---|---|
| 5 | 1 | 10 min. | n = 3 | 5.0, 5.0, 5.5 | n = 9 | All No Growth |
| 6 | 1 | 10 min. | n = 3 | 5.7, 5.7, 5.5 | n = 7 | All No Growth |
| 7 | 1 | 10 min. | n = 3 | 6.1, 5.9, 5.9 | n = 7 | All No Growth |
| | 2 | 10 min. | | 6.6, 6.5, 6.6 | n = 7 | All No Growth |
| 8 | 1 | 2 min. | n = 3 | 5.7, 5.8, 5.9 | n = 5 | All No Growth |
| | 2 | 2 min. | | | n = 5 | All No Growth |
| 9 | 4 | 2 min. | | 5.7, 5.7, 5.7 | n = 5 | All No Growth |
| | 5 | 2 min. | | | n = 5 | All No Growth |
| Potassium Sorbate | | 2 min. | | | n = 3 | 5.0, 4.9, 4.9 |
| 10 | 1 | 1 min. | n = 3 | 5.7, 5.9, 5.9 | n = 5 | All No Growth |
| | 2 | 1 min. | | | n = 5 | All No Growth |
| | 4 | 1 min. | | | n = 5 | All No Growth |
| | 5 | 1 min. | | | n = 5 | All No Growth |

Kill rates for potassium-isomerized linoleic acid prepared in house were similar to those made from starting materials from Quanao Biotech Co., Ltd., China or Stepan. USA.

Discussion

We limited these studies to surface disinfection of inanimate objects. However, cosmetically acceptable preparations of potassium-isomerized linoleic acid are used in the open market. Cosmetic uses include use on the hair, face, skin, and in the mouth, nasal cavity, and vagina (Changaris. 2020). Potassium-Isomerized Linoleic Acid Satisfies EPA Protocol for Disinfection of *Candida auris* (AR-0381) and *Candida albicans*.

We hypothesize that the conjugated diene of potassium-isomerized linoleic acid may be targeting dienophilic structures on the surfaces of microbes. If a dienophile on a microbial surface were to substantially drain the shared sp2-sp2 electrons, the two arms might rotate and "scissor" together, placing the aliphatic and carboxyl arms in contact with the microbial surface. The lethality of potassium-isomerized linoleic acid suggests that these dienophilic structures of microbial surfaces play a role in essential surface mechanisms. The targeted binding of surface dienophilic structures does not fall within known microbial patterns for development of resistance (Reygaert. 2018). Potassium-isomerized linoleic acid possesses the capacity for use against a growing number of antibiotic-resistant species, and it has been demonstrated as effective against organisms with at least 3 mechanisms of resistance (Changaris, 2018: Changaris and Sullivan. 2019). An effective disinfectant devoid of the need for hazmat precautions may be provided. The capacity of potassium-isomerized linoleic acid to effect microbial growth reduction may involve yet undiscovered or undisclosed mechanisms.

Example 2

The following Example was performed by Utah State University, Institute for Antiviral Research, Logan, Utah Procedure Virus, Media, and Cell SARS-CoV-2 virus stocks were prepared by growing virus in Vero 76 cells. Test media used was MEM supplemented with 2% FBS and 50 µg/mL gentamicin.

Virucidal Assay

A 12% ICLS was received from the sponsor in liquid form. Sample was serially diluted 2-fold in water for final test concentrations of 90%, 45%, 22.5%, and 11.3%. SARS-CoV-2 virus stock was added to triplicate tubes and media only was added to one tube of each prepared concentration to serve as toxicity controls. Ethanol was tested in parallel as a positive control and water only to serve as the virus control.

Compound and virus were incubated at room temperature for a contact time of 2 minutes. Following the contact period, the solutions were neutralized by a 1/10 dilution in test media containing 10% FBS.

Virus Quantification

Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% CO2. On day 6 post-infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.

Controls

Virus controls were tested in water and the reduction of virus in test wells compared to virus controls was calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.

Results

Virus titers and LRV of 12% ICLS against SARS-CoV-2 are shown in Table 4. Full toxicity was observed in the 1/10 and 1/100 dilutions for the 22.5%-90% samples, and in the 1/10 dilution of 11.3%. Because of this toxicity, presence of virus could not be ruled out in those wells; therefore the limit of detection for the 22.5%-90% tests was 2.7 and for the 11.3% was 1.7 log CCID50 of virus per 0.1 mL.

Virucidal activity was exhibited when 11.3% of the 12% ICLS was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%). Further testing may be warranted to evaluate activity at lower concentrations and assess reproducibility.

Neutralization controls demonstrated that residual sample did not inhibit virus growth and detection in the endpoint titer assays in wells that did not have cytotoxicity. Positive controls performed as expected, though ethanol was also toxic to cells in the 1/10 dilution, limiting the detection of virus to <1.7 log CCID50 per 0.1 mL.

TABLE 4

Virucidal efficacy of 12% ICLS against SARS-CoV-2 after incubation with virus for 2 minutes at 22 ± 2° C.

| | Concentration | Contact Time | Virus Titer[a] | LRV[b] |
|---|---|---|---|---|
| 12% ICLS | 90% | 2 minutes | <2.7 | >0.8 |
| 12% ICLS | 45% | 2 minutes | <2.7 | >0.8 |
| 12% ICLS | 22.5% | 2 minutes | <2.7 | >0.8 |
| 12% ICLS | 11.3% | 2 minutes | <1.7 | >1.8 |
| Ethanol | 63% | 2 minutes | <1.7 | >1.8 |
| Virus Control | n/a | 2 minutes | 3.5 | — |

[a]Log10 CCID50 of virus per 0.1 mL
[b]LRV (log reduction value) is the reduction of virus compared to the virus control Example 3

The following Example was performed by Utah State University, Institute for Antiviral Research, Logan, Utah Procedure Virus, Media, and Cells SARS-CoV-2 virus stocks were prepared by growing virus in Vero 76 cells. Test media used was MEM supplemented with 2% FBS and 50 µg/mL gentamicin.

Virucidal Assay

A 12% ICLS was received from the sponsor in liquid form. Sample was serially diluted 2-fold in water for final test concentrations of 90%, 45%, 22.5%, and 11.3%. SARS-CoV-2 virus stock was added to triplicate tubes and media only was added to one tube of each prepared concentration to serve as toxicity controls. Ethanol was tested in parallel as a positive control and water only to serve as the virus control.

Compound and virus were incubated at room temperature for a contact time of 2 minutes. Following the contact period, the solutions were neutralized by a 1/10 dilution in test media containing 10% FBS.

The experiment was repeated in the same way as described above testing lower concentrations of 11.3%, 1%, 0.5%, and 0.25%.

Virus Quantification

Neutralized samples were combined for quantification for the average of triplicate tests. Samples were serially diluted using eight half-log dilutions in test medium. Each dilution was added to 4 wells of a 96-well plate with 80-100% confluent Vero 76 cells. The toxicity controls were added to an additional 4 wells and 2 of these wells were infected with virus to serve as neutralization controls, ensuring that residual sample in the titer assay plated did not inhibit growth and detection of surviving virus. All plates were incubated at 37±2° C., 5% CO2. On day 6 post-infection plates were scored for presence or absence of viral cytopathic effect (CPE). The Reed-Muench method was used to determine end-point titers (50% cell culture infectious dose, CCID50) of the samples, and the log reduction value (LRV) of the compound compared to the negative (water) control was calculated.

Controls

Virus controls were tested in water and the reduction of virus in test wells compared to virus controls was calculated as the log reduction value (LRV). Toxicity controls were tested with media not containing virus to see if the samples were toxic to cells. Neutralization controls were tested to ensure that virus inactivation did not continue after the specified contact time, and that residual sample in the titer assay plates did not inhibit growth and detection of surviving virus. This was done by adding toxicity samples to titer test plates then spiking each well with a low amount of virus that would produce an observable amount of CPE during the incubation period.

Results

Virus titers and LRV of the 12% ICLS against SARS-CoV-2 are shown in Table 5. Full toxicity was observed in the ⅒ and ¹⁄₁₀₀ dilutions for the 22.5%-90% samples, and in the ⅒ dilution of 11.3%. Because of this toxicity, presence of virus could not be ruled out in those wells therefore the limit of detection for the 22.5%-90% tests was 2.7 and for the 11.3% was 1.7 log CCID50 of virus per 0.1 mL. Virucidal activity was exhibited when 11.3% 12% ICLS was incubated with virus for 2 minutes, reducing virus from 3.5 log CCID50 per 0.1 mL in virus controls to below the limit of detection of 1.7 logs (>98%). Higher concentration from 22.5%-90% also reduced virus below the limit of detection of 2.7 log CCID50 per 0.1 mL (>80%).

In the second experiment testing 12% ICLS at lower concentrations, the 11.3% sample again reduced virus from 3.7 log CCID50 per 0.1 mL below the limit of detection (<1.7 logs, >99%) and the 1% sample reduced virus titer to 1.7 log CCID50 per 0.1 mL (99%). The 0.5% and 0.25% samples did not reduce virus by >1 log.

Neutralization controls demonstrated that residual sample did not inhibit virus growth and detection in the endpoint titer assays in wells that did not have cytotoxicity. Positive controls performed as expected, though ethanol was also toxic to cells in the ⅒ dilution, limiting the detection of virus to <1.7 log CCID50 per 0.1 mL.

TABLE 5

Replicate 1 - Virucidal efficacy of 12% ICLS against SARS-CoV-2 after incubation with virus for 2 minutes at 22 ± 2° C.

|  | Concentration | Contact Time | Virus Titer[a] | LRV[b] |
|---|---|---|---|---|
| 12% ICLS | 11.3% | 2 minutes | <1.7 | >2.0 |
| 12% ICLS | 1% | 2 minutes | 1.7 | 2.0 |
| 12% ICLS | 0.5% | 2 minutes | 3.5 | 0.2 |
| 12% ICLS | 0.25% | 2 minutes | 3.3 | 0.4 |
| Ethanol | 63% | 2 minutes | <1.7 | >2.0 |
| Virus Control | n/a | 2 minutes | 3.7 | — |

[a]Log10 CCID50 of virus per 0.1 mL
[b]LRV (log reduction value) is the reduction of virus compared to the virus control

TABLE 6

| | |
|---|---|
| Cysteine-HCl | 28400 |
| D Panthenol | 31600 |
| Alanine | 40700 |
| Niacinamide | 33800 |
| Arginine | 25600 |
| Methionine | 32350 |
| Valine | 31850 |
| Phenylalanine | 130 |
| Tryptophan | 21 |
| Iso-Leucine | 29900 |
| D L Panthenol | 28650 |
| Lysine-hcl | 30700 |
| Histidine base | 28050 |
| Aspartic acid | 25100 |
| Serine | 22300 |
| Threonine | 30650 |
| Phenyl ethanol | 110 |
| Lysine base | 26900 |

The present disclosure is not to be limited in terms of the particular examples or embodiments described in this application, which are intended as illustrations of various aspects. Many modifications and variations can be made without departing from its spirit and scope, as will be apparent to those skilled in the art. Functionally equivalent materials, equipment, methods, and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular size or shape, methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of reducing the virulence of a coronavirus in a human comprising applying to the human a solution to at least one of the mouth, the nasal cavities, the lungs, the eyes, or the vagina of the human, or injecting a solution intravenously to the human, wherein the applied or injected solution comprises an effective amount of an isomerized or conjugated linoleic acid cation salt having a conjugated diene for at least a 2 log kill of the coronavirus, wherein the conjugated diene has a structure of —C=C—C=C—; and wherein the at least a log 2 kill of the coronavirus is within two minutes of the applying or injecting of the solution.

2. The method of claim 1, wherein the coronavirus comprises SARS CoV 2 (COVID 19).

3. The method of claim 1, wherein the solution further comprises at least one of water, amino acid, and alcohol.

4. The method of claim 1, wherein the solution comprises the cations at least at a molar equivalent to the conjugated diene in the solution.

5. The method of claim 1, wherein the cations are selected from the group consisting of lithium, sodium, potassium, rubidium, and combinations thereof.

6. The method of claim 1, wherein the cations are potassium.

7. The method of reducing the viruses of claim 1, wherein the cations have potassium.

8. The method of claim 4, wherein the solution comprises the cations at a molar ratio of the cations to the conjugated diene between about 1:1 and 5:1.

9. The method of claim 1, wherein the solution has a concentration of the conjugated diene between 0.1 millimolar and 500 millimolar.

10. The method of claim 9, wherein the solution has a concentration of the conjugated diene between 0.2 millimolar and 60 millimolar.

11. A method of sanitizing or disinfecting a surface, area, object, or porous or non-porous material contaminated by a coronavirus, comprising applying a solution comprising an effective amount of an isomerized or conjugated linoleic acid cation salt having a conjugated diene with a structure of —C═C—C═C— to the surface, the area, the object, or the porous or non-porous material, wherein the solution comprising an effective amount of the isomerized or conjugated linoleic acid cation salt having the conjugated diene for at least a 2 log kill of coronavirus within two minutes of the applying of the solution.

12. The method of claim 11, wherein the coronavirus comprises SARS CoV 2 (COVID-19) and the application of the solution reduces the virulence of SARS CoV 2 (COVID-19).

13. The method of claim 11, wherein the solution further comprises at least one of water, amino acid, and alcohol.

14. The method of claim 11, wherein the solution comprises the cations at least at a molar equivalent to the conjugated diene in the solution.

15. The method of claim 11, wherein the cations are selected from the group consisting of lithium, sodium, potassium, rubidium, and combinations thereof.

16. The method of claim 11, wherein the cations are potassium.

17. The method of claim 14, wherein the solution comprises the cations at a molar ratio of the cations to the conjugated diene between about 1:1 and 5:1.

18. The method of claim 11, wherein the solution has a concentration of the conjugated diene between 0.1 millimolar and 500 millimolar.

* * * * *